United States Patent [19]

Di Battista et al.

[11] Patent Number: 4,772,708
[45] Date of Patent: Sep. 20, 1988

[54] DERIVATIVES OF ALKYL-SUBSTITUTED 4-HYDROXY-METHYL-PIPERIDINE

[75] Inventors: Piero Di Battista; Gilberto Nucida, both of Milan, Italy

[73] Assignee: Ausimont S.p.A., Milan, Italy

[21] Appl. No.: 28,039

[22] Filed: Mar. 20, 1987

Related U.S. Application Data

[63] Continuation of Ser. No. 736,328, May 21, 1985, abandoned.

[30] Foreign Application Priority Data

May 22, 1984 [IT] Italy .................. 21034 A/84

[51] Int. Cl.[4] .................. C07D 211/94; C08K 5/34
[52] U.S. Cl. .................. 546/5; 546/13; 546/14; 546/16; 546/22; 546/187; 546/190; 546/248; 548/209; 548/212; 524/100; 524/102; 524/99
[58] Field of Search .................. 546/5, 13, 14, 16, 22, 546/186, 187, 190, 248; 544/209, 212

[56] References Cited

U.S. PATENT DOCUMENTS 3,840,494 10/1974 Murayama et al. .................. 546/16

Primary Examiner—Robert T. Bond
Attorney, Agent, or Firm—Stevens, Davis, Miller & Mosher

[57] ABSTRACT

Derivatives of 4-hydroxy-methyl-piperidine having general formula:

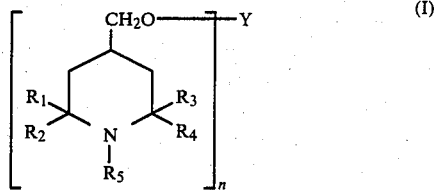

wherein: $R_1$, $R_2$, $R_3$ and $R_4$ may be alkyl or may form, with the carbon they are bound to, a cycloalkyl group or the group

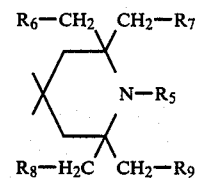

with $R_6$, $R_7$, $R_8$ and $R_9$ being hydrogen or alkyl; $R_5$ may be H, alkyl, aryl, alkenyl, etc.; Y may be an organic or inorganic group or atom having a valence from 1 to 4 and n is an integer from 1 to 4.

The use of the derivatives of the alkyl-substituted 4-hydroxy-methyl-piperidine of formula (I) as stabilizers of polymeric substances, and polymeric compositions stabilized with said piperdine derivatives.

This invention relates to new derivatives of alkyl-substituted 4-hydroxy-methyl-piperidine, to the use thereof as stabilizers of polymeric substances usually subject to worsening owing to thermal and/or photo-oxidation, and to the polymeric compositions stabilized with said derivatives.

19 Claims, No Drawings

DERIVATIVES OF ALKYL-SUBSTITUTED 4-HYDROXY-METHYL-PIPERIDINE

This application is a continuation of application Ser. No. 736,328, filed May 21, 1985.

BACKGROUND OF THE INVENTION

As is known, heat, oxygen and light, especially the actinic radiations existing in the low wave-length ultraviolet band, do badly affect the appearance and the properties of the organic polymers. For example, the polyesters, which are usually colorless, yellow when exposed to sunlight. Analogously, the oxidizing rate of polyolefins when exposed to air is highly increased due to ultraviolet light; polystyrene gets yellow and brittle, with corresponding loss of its desirable properties, when exposed to actinic light, etc. The same degradation and alteration effects of the mechanical properties occur when the polymeric materials are subjected to heat-treatments, as happens for example during their transformation into formed articles, such as films, fibers and the like.

With a view to stabilizing the polymeric materials and to retaining unaltered the properties thereof, it is a usual practice to add to them one or more stabilizers, the function of which is just that of opposing the susceptibility of such materials of undergoing an oxidative and thermal degradation.

A particular type of stabilizers which has been very successful are the stereically hindered amines (HALS) and in particular the derivatives of alkyl-substituted piperidine.

The hingered amines based on alkyl-substituted piperidine, though being excellent stabilizers for polymeric substances generally subject to worsening, are not suited to be utilized, with the same results, in all polymeric substances and for all technological uses. In fact, the known stabilizers are affected by the drawback of not possessing all those parameters and technical characteristics necessary for all the technological applications, such as low volatility, resistance to migration, thermal stability, insolubility in water, etc.

Thus, it is an object of the present invention to improve the properties of the known stabilizers containing the radical of alkyl-substituted piperidine.

It has now been found that this and still further objects are achieved by derivatives of alkyl-substituted 4-hydroxy-methyl-piperidine having general formula:

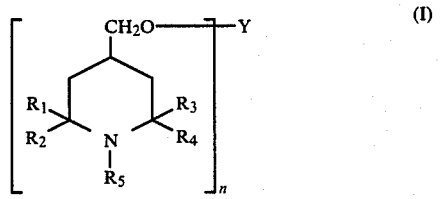

in which:

$R_1$, $R_2$, $R_3$ and $R_4$, which may be like or unlike one another, are each a lower alkyl group, or $R_1$ and $R_2$ and/or $R_3$ and $R_4$, along with a carbon atom which they are bound to, represent a cyclo-alkyl group or a group of formula:

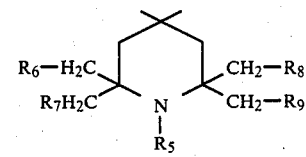

in which $R_6$, $R_7$, $R_8$ and $R_9$, which may be like or unlike one another, are a hydrogen atom or a lower alkyl group and $R_5$ has the meaning specified hereinbelow;

$R_5$ is a hydrogen atom, an alkyl group, an alkenyl group, an alkoxyalkyl group, an aralkyl group, either non-substituted or carrying one or more substituents on the aryl radical, a 2,3-epoxypropyl group, a group of formula —$CH_2$—$COOR_{10}$ (in which $R_{10}$ is an alkyl group, an alkenyl group, an aralkyl group or a cyclohexyl group), a group of formula:

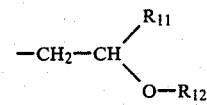

(in which $R_{11}$ is a hydrogen atom, a methyl group, an ethyl group or a phenyl group and $R_{12}$ is a hydrogen atom, an alkyl-substituted piperidyl group, a triazinyl group or an acyl group), an aliphatic acyl group or a group of formula —$COOR_{13}$ (in which $R_{13}$ is an alkyl group, a benzyl group or a phenyl group);

Y represents an organic or inorganic group or atom having a valence of from 1 to 4 which does not adversely affect the stabilizing activity of the polymer; and n is an integer from 1 to 4, depending on the valence of Y.

According to the present invention it has been also found that the derivatives of alkyl-substituted 4-hydroxy-methyl-piperidine having general formula (I), either alone or in admixture with other known stabilizers, can efficaciously stabilize a wide range of polymers against photo and thermal degradation and, furthermore, they are highly compatible with the polymers, in particular with polyolefins.

The term "lower alkyl", whenever used herein and in the annexed claims, means an alkyl containing from 1 to 6 carbon atoms, extremes included.

In above-reported formula (I), when $R_1$, $R_2$, $R_3$ or $R_4$ represents an alkyl group, this may be preferably an alkyl group containing from 1 to 4 carbon atoms, such as, e.g., methyl, ethyl, propyl, isopropyl, butyl or isobutyl, the methyl group being preferred.

$R_1$ and $R_2$ and/or $R_3$ and $R_4$, along with the carbon atom on which they are bound, may represent a cycloalkyl group containing from 5 to 7 carbon atoms, such as, e.g., cyclopentyl, cyclohexyl, cycloheptyl, etc., or an alkyl-substituted piperidyl group, such as for example:

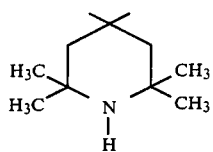

When R₅ is an alkyl group, it may contain from 1 to 8 carbon atoms. In practice, it is preferable that the alkyl group contain from 1 to 4 carbon atoms and among these, the methyl group is particularly preferred.

When R₅ is an alkenyl group, it may contain from 3 to 6 carbon atoms, such as e.g., the allyl group, the 2-butenyl group or the 2-hexenyl group; the alkenyl group containing 3 or 4 carbon atoms is the preferred one, and among said groups the allyl group is particularly preferred.

When R₅ is an alkoxyalkyl group, it may be an alkoxyalkyl group containing 1 to 3 carbon atoms in the alkyl chain and from 1 to 18 carbon atoms in the alkoxyl chain.

Examples of alkoxyalkyl groups are: methoxymethyl, ethoxymethyl, 2-butoxyethyl, 3-butoxypropyl, 2-octoxyethyl, 2-octadecyloxyethyl. Of the alkoxy-alkyl groups, those containing on the whole 2 to 6 carbo-atoms are preferred.

When R₅ is an aralkyl group, it may preferably contain 7 or 8 carbon atoms and it may be unsubstituted or it may contain up to 3 substituents on the alkyl radical. Chlorine atoms, alkyl groups with 1 to 4 carbon atoms, alkoxy groups with 1 to 8 carbon atoms or hydroxy groups may be used as substituents. Typical examples of aralkyl groups are: benzyl, p.chlorobenzyl o.chlorobenzyl, m.chlorobenzyl, o.methylbenzyl, m.methylbenzyl, p.methylbenzyl, p.isopropylbenzyl, p.ter.butylbenzyl, p.methoxybenzyl, p.butoxybenzyl, p.octoxybenzyl, 4-hydroxy-3,5-di-ter. butylbenzyl, etc.

When R₅ represents a group of formula —CH₂—COOR₁₀, R₁₀ may represent:
  an alkyl group containing preferably from 1 to 18 carbon atoms, such as methyl, ethyl, isopropyl, butyl, isobutyl, t.butyl, isopentyl, octyl, dodecyl, octadecyl, etc.;
  an alkenyl group preferably containing from 3 to 6 carbon atoms, such as allyl, 2-butenyl, 2-hexyl, etc.;
  a phenyl group;
  an aralkyl group, preferably containing 7 or 8 carbon atoms, or
  a cyclohexyl group; the alkyl group containing 1 to 4 carbon atoms being the preferred one.

When R₅ represents the group

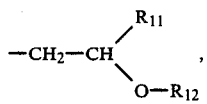

R₁₁ represents a hydrogen atom, a methyl group or a phenyl group and R₁₂ represents a hydrogen atom, an acyl group, for example an acyl aliphatic, araliphatic, aromatic or alicyclic group, an alkyl-substituted piperidyl group, such as:

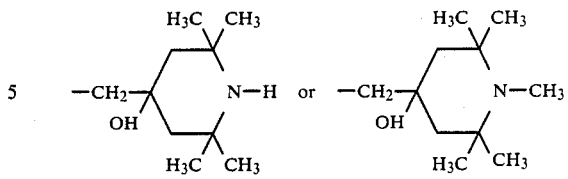

or a triazinic group, such as:

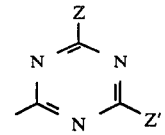

in which Z and Z', which may be like or unlike each other, represent hydrogen, —NR₁₄R₁₅, —O—R₁₆ or —S—R₁₇ in which R₁₄, R₁₅, R₁₆ and R₁₇ may be hydrogen, an alkyl radical containing from 1 to 18 carbon atoms or an alkyl-substituted piperidyl group such as:

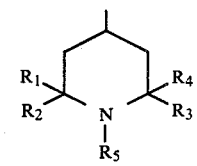

or R₁₄ and R₁₅ along with the N atom form together a cycle either or not containing other heteroatoms such as:

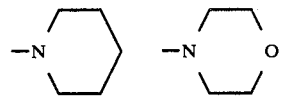

When R₁₂ is an acyl group, this has preferably the formula —COR₁₈ in which R₁₈ is an alkyl group with 1 to 18 carbon atoms; an alkenyl group with from 2 to 4 carbon atoms; a phenyl group, which may be either non-substituted or substituted with up to 3 substituents, equal or different, selected from among chlorine, alkyl with 1 to 4 carbon atoms, alkoxy with 1 to 8 carbon atoms or hydroxy; an aralkyl group with 7 or 8 carbon atoms, the aryl radical of which may be non-substituted or substituted with up to 3 substituents, like or different from one another, selected from among chlorine, alkyl with 1 to 4 carbon atoms, alkoxy with 1 to 6 carbon atoms or hydroxy; a styryl group, or a cyclohexyl group.

Examples of radicals R₁₈ are: methyl, ethyl, propyl, butyl, heptyl, 1-ethyl-pentyl, nonyl, undecyl, heptadecyl, vinyl, 1-propenyl; 2-methyl-1-propenyl, 1-butenyl, phenyl, o.chlorophenyl, m.chlorophenyl, 2,4-dichlorophenyl, o.methylphenyl, p.methylphenyl, m.methylphenyl, p.isopropylphenyl, p.ter.butylphenyl, p.methoxyphenyl, p.ethoxyphenyl, p.butoxyphenyl, 3,4,5-trimethoxyphenyl, o.hydroxyphenyl, 4-hydroxy-3,5-di-ter. butylphenyl, benzyl, p.methylbenzyl, 4-hydroxy-3,5-di-ter. butylphenyl.

Particularly preferred are the groups of formula —CH₂—CH₂—O—R₁₂, in which R₁₂ has one of the values cited hereinbefore.

When $R_5$ is an aliphatic acyl group, it may preferably contain up to 4 carbon atoms and it is preferably a saturated or unsaturated acyl group, such as e.g., the formyl, acetyl, acrylyl or crotonyl groups.

When $R_5$ is a group of formula —COOR$_{13}$, $R_{13}$ is an alkyl group, preferably with 1 to 8 carbon atoms, such as methyl, ethyl, isobutyl, heptyl; a benzyl group or a phenyl group.

Generally speaking, group Y represents a hydrogen atom, a hydrocarbon residue which may be non-substituted or substituted, a residue deriving from an organic or inorganic acid, a heterocyclic group, an atom of phosphorus or of boron or of silicon. In particular, the following groups are the preferred ones:

When n=1
Y preferably represents:
a hydrogen atom;
an acyl-aliphatic, aryl-aliphatic, alicyclic, aromatic or heterocyclic group, preferably an acyl group containing up to 18 carbon atoms and, even better, a group of formula —COR$_{19}$ in which R$_{19}$ represents a hydrogen atom; an alkyl group with 1 to 17 carbon atoms (such as methyl, ethyl, propyl, isopropyl, butyl, ter.butyl, pentyl, isopentyl, 1-ethylpentyl, nonyl, undecyl, pentadecyl, etc.); an alkenyl group with 2 to 5 carbon atoms, such as vinyl, 1-propenyl, 2-methyl-1-propenyl, isopropenyl, or 1,3-pentadienyl; an alkynyl group with 2 or 3 carbon atoms, such as ethynyl or propynyl; a phenyl group either non-substituted or substituted with up to 3 substituents either like or unlike, such as chlorine, alkyl with 1 to 4 carbon atoms, alkoxy with 1 to 8 carbon atoms, hydroxy or nitro (such as for example phenyl, o.chlorophenyl, m.chlorophenyl, p.chlorophenyl, o.methylphenyl, m.methylphenyl, p.methylphenyl, p.isopropylphenyl, p.ter.butylphenyl, m.methoxyphenyl, p.methoxyphenyl, p.octoxyphenyl, o.hydroxyphenyl, 2-hydroxy-3-methylphenyl, 4-hydroxy-3,5-di-ter.butylphenyl, m.nitrophenyl, etc.); a naphthyl group; a styryl group; an aralkyl group with 7–8 carbon atoms, which may be non-substituted or substituted with up to 3 like or unlike substituents such as chlorine, alkyl with 1–4 carbon atoms, alkoxy with 1 to 8 carbon atoms or hydroxy (such as benzyl, phenethyl, 4-hydroxy-3,5-di-ter.butylbenzyl or 4-hydroxy-3,5-di-ter.butylphenethyl); a phenoxymethyl group; a cyclohexyl group; a 2-pyridyl group; a 3pyridyl group; a 4-pyridyl group; a 2-furyl group;
a group of formula —CO—R$_{20}$—COOH, in which R$_{20}$ is an alkylene group preferably containing from 1 to 10 carbon atoms, the chain of which can be interrupted by an atom of oxygen or of sulphur; or a metal salt thereof in which the metal may be, for example, barium, nickel, manganese, calcium, zinc, iron, sodium, cobalt or tin; or a lower alkyl ester thereof in which the alkyl chain contains from 1 to 4 carbon atoms, such as the methyl, ethyl, propyl, butyl esters, etc.;
a radical obtained from the removal of a hydroxy group of a phosphorus acid, for example a radical of phosphoric acid, of phosphonic acid, or phosphorous acid, either simple or substituted such as the radicals

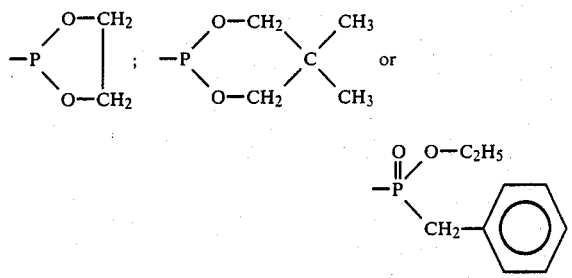

a group of formula:

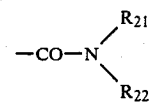

in which R$_{21}$ is hydrogen; an alkyl group containing 1 to 4 carbon atoms; an aralkyl group preferably containing 7 or 8 carbon atoms; a phenyl group; and R$_{22}$ is an alkyl group containing from 1 to 18 carbon atoms, an aryl group preferably containing 6 to 10 carbon atoms, optionally substituted by one or more chlorine atoms and/or alkyl groups with from 1 to 4 carbon atoms, such as for example phenyl, o.chlorophenyl, p.chlorophenyl, o., m. and p.toluyl, alpha-naphthyl or beta-naphthyl; an aralkyl group containing 7 or 8 carbon atoms, or a cyclohexyl group. As an alternative, R$_{21}$ and R$_{22}$, together and with the nitrogen atom to which they are bound, represent a piperidine group, a 1-pyrrolidinyl group or a morpholine group. Among these groups, those having formula —CO—N-H—R$_{22}$, in which R$_{22}$ is the same as specified hereinbefore, are particularly preferred;
an alkyl group preferably containing from 1 to 18 carbon atoms, such as methyl, ethyl, butyl, octyl, dodecyl or octadecyl;
an alkynyl group preferably containing from 3 to 6 carbon atoms, such as allyl, 2-butenyl, methallyl or 2-hexenyl;
an aralkyl group with from 7 to 9 carbon atoms and optionally carrying up to 3 substituents in the aryl chain, such as an alkyl with from 1 to 4 carbon atoms and/or a hydroxy, such as for example benzyl, p.methylbenzyl, p.isopropylbenzyl; 4-hydroxy-3,5-di-ter.butylbenzyl or 3-(4-hydroxy-3,5-di-ter.butylphenyl)-propyl;
a cyclohexyl group;
a group of formula

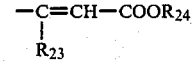

in which R$_{23}$ is a hydrogen atom, a methyl or lower alkyl group or a phenyl group and R$_{24}$ an alkyl group containing preferably from 1 to 8 carbon atoms.

When n=2
Y represents:
an aliphatic, araliphatic, aromatic, alicyclic or heterocyclic diacyl, preferably containing up to 12 carbon atoms and, preferably a group of formula —CO—(R$_{25}$)$_m$—CO— in which m may be 0 or 1 and R$_{25}$ an alkylene group with 1 to 20 carbon atoms either linear or ramified, optionally containing the alkylbenzyl or hydroxy-alkylbenzyl group, and the chain of which may be interrupted by an atom of sulphur or of oxygen; an alkylene group with from 2 to 4 carbon atoms; a phenylene group, a cyclohexylene group; a 2-4-pyridindiyl group, a 2,5-pyridindiyl group or a thiophendiyl group;

a carbonyl group;

a group obtained by removing the two hydroxyl groups of an acid containing phosphorus, in particular a group of formula:

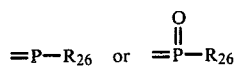

in which R$_{26}$ represents a hydrogen atom; an alkyl group with preferably from 1 to 4 carbon atoms; a phenyl or benzyl group, optionally substituted, such as 4-hydroxy-3,5-di-tertbutylbenzyl;

a group of formula:

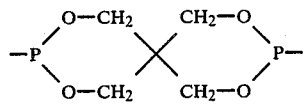

a group of formula:

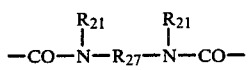

in which R$_{21}$ is the same as indicated hereinabove and R$_{27}$ represents an alkylene group preferably containing from 2 to 10 carbon atoms; an arylene group having preferably from 6 to 10 carbon atoms and optionally substituted such as o.phenylene, m.phenylene, p.phenylene, 2,4-toluidene, 1,5-naphthylene, etc., a xylylene group, a cyclohexylene group such as 1,4-cyclohexylene, a group of formula:

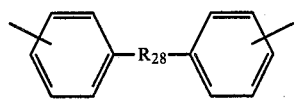

in which R$_{28}$ may be an oxygen atom of an alkylene group containing from 1 to 4 carbon atoms;

a group of formula:

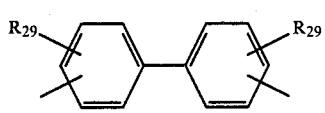

in which R$_{29}$ may be a hydrogen atom of a methyl group, a group of formula:

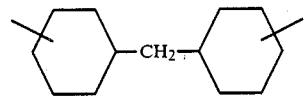

such as methylene-di-4,1-cyclohexene, or a group of formula:

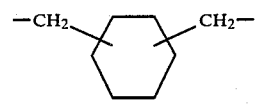

such as for example 1,3-cyclohexylene-dimethylene, etc.; among the groups comprised in this formula, those of formula —CO—NH—R$_{27}$—NH—CO—, in which R$_{27}$ has the values defined hereinbefore, are the preferred;

an alkylene group containing up to 10 carbon atoms and preferably from 2 to 6 carbon atoms, such as ethylene, tetramethylene, hexamethylene, etc.;

an alkenylene group containing from 4 to 10 carbon atoms;

or a xylylene group, such as o.xylylene, m.xylylene, p.xylylene, etc.

When n=3

Y may be selected from the following radicals:

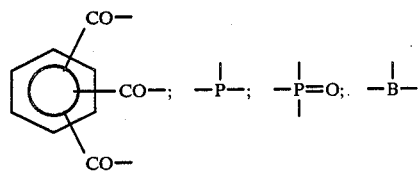

When n=4

Y may be:

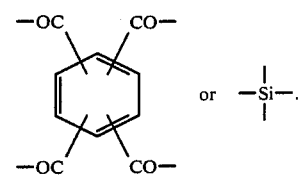

The derivatives of the alkyl-substituted 4-hydroxypiperidine which are particularly preferred are those of general formula:

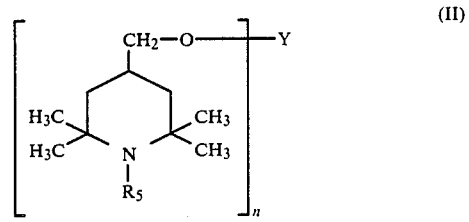

(II)

in which R$_5$ is a hydrogen atom, a methyl group, a benzyl group, a 2,3-opoxypropyl group or a group of formula —CH$_2$—CH$_2$—O—R$_{12}$, in which R$_{12}$ is hydrogen or an alkyl group with from 2 to 18 carbon atoms or a benzoyl group; n=1, 2 or 3; and when n=1

Y represents a group of formula —CO—$R_{19}$ in which $R_{19}$ represents an alkyl group with from 1 to 17 carbon atoms, a phenyl group optionally substituted by up to 3 alkyl radicals with from 1 to 4 carbon atoms and/or a hydroxy radical, or a 4-hydroxy-3,5-ditert.butyl-phenethyl; or a group of formula —CO—NH—$R_{22}$ in which $R_{22}$ represents an alkyl group with from 1 to 18 carbon atoms, a phenyl group or a cyclohexyl group;

when n=2

Y represents a group of formula —CO—($R_{25}$)$_m$—CO— in which m is 0 or 1 and $R_{27}$ represents an alkenyl group with 1 to 10 carbon atoms, the group —CH$_2$—CH$_2$—S—CH$_2$—CH$_2$ or a phenylene group, a group of formula

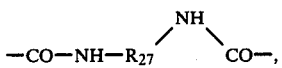

in which $R_{27}$ represents the hexamethylene radical, the 2,4-toluilene radical or the methylene-di-p.phenylene radical;

when n=3
Y represents

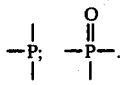

The particularly preferred compounds are those in which n=1 and Y represents a group of formula —CO—$R_{19}$; or n=2 and Y represents a group of formula —CO—$R_{25}$—CO—, with $R_{19}$ and $R_{25}$ having the values defined hereinbefore.

A non-limitative list of derivatives of alkyl-substituted 4-hydroxy-methyl-piperidine is given hereinbelow, and the numbers which refer to the products will be utilized to identify them also in the examples.

(1) (2,2,6,6-tetramethyl)-4-hydroxymethyl piperidine;
(2) (2,2,6,6-tetramethyl)-4-methyl piperidine acetate;
(3) (2,2,6,6-tetramethyl)-4-methyl piperidine palmitate;
(4) (2,2,6,6-tetramethyl)-4-methyl piperidine ethylhexanoate;
(5) (2,2,6,6-tetramethyl)-4-methyl piperidine stearate;
(6) (2,2,6,6-tetramethyl)-4-methyl piperidine acrylate;
(7) (2,2,6,6-tetramethyl)-4-methyl piperidine crotonate;
(8) (2,2,6,6-tetramethyl)-4-methyl piperidine methacrylate;
(9) (2,2,6,6-tetramethyl)-4-methyl piperidine tetrolate;
(10) (2,2,6,6-tetramethyl)-4-methyl piperidine benzoate;
(11) (2,2,6,6-tetramethyl)-4-methyl piperidine p.tert.butylbenzoate;
(12) (2,2,6,6-tetramethyl)-4-methyl piperidine p-methoxybenzoate;
(13) (2,2,6,6-tetramethyl)-4-methyl piperidine salicylate;
(14) (2,2,6,6-tetramethyl)-4-methyl piperidine p.chlorobenzoate;
(15) (2,2,6,6-tetramethyl)-4-methyl piperidine naphthalene-1-carboxylate;
(16) (2,2,6,6-tetramethyl)-4-methyl piperidine phenyl acetate;
(17) (2,2,6,6-tetramethyl)-4-methyl piperidine β-(4-hydroxy-3,5-ditertbutylphenyl)-propionate;
(18) (2,2,6,6-tetramethyl)-4-methyl piperidine cinnamate;
(19) (2,2,6,6-tetramethyl)-4-methyl piperidine cyclohexancarboxylate;
(20) (2,2,6,6-tetramethyl)-4-methyl piperidine methyl salicylate;
(21) (2,2,6,6-tetramethyl)-4-methyl piperidine methylphthalate;
(22) (1,2,2,6,6-pentamethyl)-4-hydroxymethyl piperidine;
(23) (1,2,2,6,6-pentamethyl)-4-methyl-piperidine stearate;
(24) (1,2,2,6,6-pentamethyl)-4-methyl piperidine benzoate;
(25) (1,2,2,6,6-pentamethyl)-4-methyl piperidine m.toluate;
(26) (1,2,2,6,6-pentamethyl)-4-methyl piperidine p.octyloxybenzoate;
(27) (1,2,2,6,6-pentamethyl)-4-methyl piperidine β-(4-hydroxy-3,5-di-tertbutylphenyl)propionate;
(28) (1-butyl-2,2,6,6-tetramethyl)-4-methyl piperidine hexanoate;
(29) (1-allyl-2,2,6,6-tetramethyl)-4-methyl piperidine stearate;
(30) (1,allyl-2,2,6,6-tetramethyl)-4-methyl piperidine crotonate;
(31) (1-allyl-2,2,6,6-tetramethyl)-4-methyl piperidine benzoate;
(32) (1-benzyl-2,2,6,6-tetramethyl)-4-methyl piperidine acetate;
(33) (1-benzyl-2,2,6,6-tetramethyl)-4-methyl piperidine stearate;
(34) (1-benzyl-2,2,6,6-tetramethyl)-4-methyl piperidine crotonate;
(35) (1-benzyl-2,2,6,6-tetramethyl)-4-methyl piperidine benzoate;
(36) [1(2,3-epoxypropyl)2,2,6,6-tetramethyl]-4-methyl piperidine stearate;
(37) [1(2,3-epoxypropyl)2,2,6,6-tetramethyl]-4-methyl piperidine benzoate;
(38) 1-(2-hydroxyethyl)2,2,6,6-tetramethyl-4-hydroxy methyl piperidine;
(39) [1(2-hydroxyethyl)2,2,6,6-tetramethyl]-4-methyl piperidine benzoate;
(40) [1(2-hydroxypropyl)2,2,6,6-tetramethyl]-4-methyl piperidine benzoate;
(41) 1(2-hydroxy-2-phenylethyl)2,2,6,6-tetramethyl-4-methyl piperidine p.tertbutylbenzoate;
(42) [1(2-acetoxymethyl)2,2,6,6-tetramethyl]-4-methyl piperidine benzoate;
(43) [1(2-stearoyloxyethyl)2,2,6,6-tetramethyl]-4-methyl piperidine stearate;
(44) 1-{2[β-(4-hydroxy-3,5-ditertbutylphenyl)propionyloxy]ethyl}2,2,6,6-tetramethyl-4-methyl piperidine β(4-hydroxy-3,5-di-tertbutyl phenyl)propionate;
(45) [1-(2-palmitoxyethyl)-2,2,6,6-tetramethyl]-4-methyl piperidine palmitate;
(46) [1-2-acetoxypropyl]-2,2,6,6-tetramethyl]-4-methyl piperidine benzoate;
(47) [1-(2-acetoxy-2-phenylethyl)-2,2,6,6-tetramethyl]-4-methyl piperidine butyrate;
(48) (1-ethoxymethyl-2,2,6,6-tetramethyl)-4-methyl piperidine benzoate;
(49) (1-butoxyethyl-2,2,6,6-tetramethyl)-4-methyl piperidine butyrate;
(50) (1-formyl-2,2,6,6-tetramethyl)-4-methyl piperidine butyrate;

(51) (1-acetyl-2,2,6,6-tetramethyl)-4-methyl piperidine benzoate;
(52) (2,2,6,6-tetramethyl)-4-methyl piperidine methyl carbamate;
(53) (2,2,6,6-tetramethyl)-4-methyl piperidine octadecyl carbamate;
(54) (2,2,6,6-tetramethyl)-4-methyl piperidine carbanilate;
(55) (2,2,6,6-tetramethyl)-4-methyl piperidine p.chlorocarbanilate;
(56) (2,2,6,6-tetramethyl)-4-methyl piperidine 1-naphthalene carbamate;
(57) (2,2,6,6-tetramethyl)-4-methyl piperidine cyclohexane carbamate;
(58) (2,2,6,6-tetramethyl)-4-methyl piperidine piperidin-1-carboxylate;
(59) (2,2,6,6-tetramethyl)-4-methyl piperidine pyrrolidin-1-carboxylate;
(60) (1,2,2,6,6-pentamethyl)-4-methyl piperidine methylcarbamate;
(61) (1,2,2,6,6-pentamethyl)-4-methyl piperidine carbanilate;
(62) (1-butyl 2,2,6,6-tetramethyl)-4-methyl piperidine methyl carbamate;
(63) (1-benzyl 2,2,6,6-tetramethyl)-4-methyl piperidine methyl carbamate;
(64) [1-(2-hydroxyethyl)-2,2,6,6-tetramethyl]-4-methyl piperidine cyclohexane carbamate;
(65) [1-(2-acetonyl ethyl)-2,2,6,6-tetramethyl]-4-methyl piperidine methyl carbamate;
(66) (2,2,6,6-tetramethyl)-4-methoxymethyl piperidine;
(67) 4-butoxymethyl-(2,2,6,6-tetramethyl) piperidine;
(68) 4-octadecyloxymethyl-(2,2,6,6-tetramethyl) piperidine;
(69) [(2,2,6,6-tetramethyl-4-hydroxy)-4-piperidine methoxy](2,2,6,6-tetramethyl)-4-methylpiperidine;
(70) β[(2,2,6,6-tetramethyl)-4-piperidine methoxy]ethyl acrylate;
(71) (1,2,2,6,6-pentamethyl)-4-methoxymethyl piperidine;
(72) 4-benzyloxymethyl-(1,2,2,6,6-pentamethyl)piperidine;
(73) 1-allyl2,2,6,6-tetramethyl-4-allyloxymethyl piperidine;
(74) 1-(2-hydroxymethyl)-4-methoxymethyl(2,2,6,6-tetramethyl)piperidine;
(75) 1-(2-acetoxyethyl)-4-methoxymethyl(2,2,6,6-tetramethyl)piperidine;
(76) bis-(2,2,6,6-tetramethyl)-4-methyl piperidine carbonate;
(77) bis-(2,2,6,6-tetramethyl)-4-methyl piperidine oxalate;
(78) bis-(2,2,6,6-tetramethyl)-4-methyl piperidine succinate;
(79) bis-(2,2,6,6-tetramethyl)-4-methyl piperidine adipate;
(80) bis-(2,2,6,6-tetramethyl)-4-methyl piperidine sebacate;
(81) bis-(2,2,6,6-tetramethyl)-4-methyl piperidine (3,5-di-tertbutyl-4-hydroxy)benzyl, n.butyl malonate;
(82) bis-(2,2,6,6-tetramethyl)-4-methyl piperidine diethyl malonate;
(83) bis-(2,4,6,6-tetramethyl)-4-methyl piperidine fumarate
(84) bis-(2,2,6,6-tetramethyl)-4-methyl piperidine terephthalate;
(85) bis-(2,2,6,6-tetramethyl)-4-methyl piperidine cyclohexane 1,4-dicarboxylate;
(86) bis-(2,2,6,6-tetramethyl)-4-methyl piperidine phenyl phosphonate;
(87) bis-(1,2,2,6,6-pentamethyl)-4-methyl piperidine adipate;
(88) bis-(1,2,2,6,6-pentamethyl)-4-methyl piperidine sebacate;
(89) bis-(1,2,2,6,6-pentamethyl)-4-methyl piperidine terephthalate;
(90) mono-(1,2,2,6,6-pentamethyl)-4-methyl piperidine succinate;
(91) mono-(1,2,2,6,6-pentamethyl)-4-methyl piperidine 3,4,5,6-tetrahydrophthalate;
(92) mono-(2,2,6,6-tetramethyl)-4-methyl piperidine maleate;
(93) nickel di-[3,4,5,6-tetrahydrophthalate of mono-(1,2,2,6,6-pentamethyl)-4-methyl piperidine];
(94) calcium di-[adipate of mono-(1,2,2,6,6-pentamethyl)-4-methyl piperidine];
(95) zinc di-[succinate of mono-(2,2,6,6-tetramethyl)-4-methyl piperidine];
(96) barium di-[succinate of mono-2,2,6,6-tetramethyl)-4-methyl piperidine];
(97) nickel di-[maleate of mono-(2,2,6,6-tetramethyl)-4-methyl piperidine];
(98) nickel di-[succinate of mono-(1,2,2,6,6-pentamethyl)-4-methyl piperidine];
(99) bis{[1-(2,3-epoxypropyl) 2,2,6,6-tetramethyl]-4-methyl piperidine}isophthalate;
(100) bis[(1-benzyl-2,2,6,6-tetramethyl)-4-methyl piperidine]sebacate;
(101) bis{[1-(-acetoxyethyl) 2,2,6,6-tetramethyl]-4-methyl piperidine}sebacate;
(102) bis[(2,2,6,6-tetramethyl)-4-methyl piperidine]hexamethylene-di-carbamate;
(103) bis[(2,2,6,6-tetramethyl)-4-methyl piperidine]toluene-2,4-di-carbamate;
(104) bis[(2,2,6,6-tetramethyl)-4-methyl piperidine]-naphthalene-1,5-di-carbamate;
(105) bis[(2,2,6,6-tetramethyl)-4-methyl piperidine](oxy di-p.phenylene)di-carbamate;
(106) bis[(2,2,6,6-tetramethyl)-4-methyl piperidine](-methylene-di-p.phenylene)di-carbamate;
(107) bis[(2,2,6,6-tetramethyl)-4-methyl piperidine](-methylene-di-4,1-cyclohexylene)-di-carbamate;
(108) bis[(1,2,2,6,6-pentamethyl)-4-methyl piperidine]-hexamethylene-di-carbamate;
(109) bis[(1,2,2,6,6-pentamethyl)-4-methyl piperidine]-methylene-di-p.phenylene-di-carbamate;
(110) 1,2bis[(2,2,6,6-tetramethyl)-4-piperidine methoxy]ethane;
(111) 1,4bis[(2,2,6,6-tetramethyl)-4-piperidine methoxy]butane;
(112) 1,4bis[(2,2,6,6-tetramethyl)-4-piperidine methoxy]butene;
(113) 1,6bis[(2,2,6,6-tetramethyl)-4-piperidine methoxy]hexane;
(114) 1,4bis[(2,2,6,6-tetramethyl)-4-piperidine methoxy]methylbenzene;
(115) 1,3bis{[(1,2,2,6,6-pentamethyl)-4-piperidine methoxy]methyl}benzene;
(116) 1,6bis{[1-(2-stearoyloxyethyl) 2,2,6,6-tetramethyl]-4-piperidine methoxy}hexane;
(117) the compound:

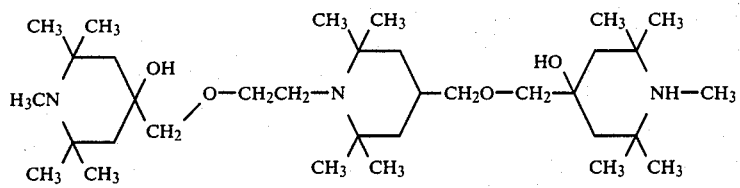

(118) tris[(2,2,6,6-tetramethyl)-4-methyl piperidine]-trimellitate;
(119) tris[(2,2,6,6-tetramethyl)-4-methyl piperidine]-trimesate;
(120) tris[(2,2,6,6-tetramethyl)-4-methyl piperidine]tricarballylate;
(121) tris[(2,2,6,6-tetramethyl)-4-methyl piperidine]-phosphite;
(122) tris[(2,2,6,6-tetramethyl)-4-methyl piperidine]-phosphate;
(123) tris[(1,2,2,6,6-pentamethyl)-4-methyl piperidine]-trimellitate;
(124) tris[(1,2,2,6,6-pentamethyl)-4-methyl piperidine]-phosphite;
(125) tetrakis[(2,2,6,6-tetramethyl)-4-methyl piperidine]pyromellitate;
(126) tetrakis[(1,2,2,6,6-pentamethyl)-4-methyl piperidine]pyromellitate;
(127) (2,5-dioxa-1-phospholan-1-yloxy)-[(2,2,6,6-tetramethyl)-4-methyl piperidine];
(128) (4,4-dimethyl-2,6-dioxa-1-phospholan-1-yloxy)[(2,2,6,6-tetramethyl)-4-methyl piperidine];
(129) O-ethyl O-[(2,2,6,6-tetramethyl)-4-methyl piperidine]benzyl phosphonate;
(130) O,O′-bis[(2,2,6,6-tetramethyl)-4-methyl piperidine]phosphonate;
(131) O,O′-bis[(2,2,6,6-tetramethyl)-4-methyl piperidine]benzyl phosphonate;
(132) O,O′-bis-[(2,2,6,6-tetramethyl)-4-methyl piperidine]4-hydroxy-3,5-di-tertbutyl benzyl phosphonate;
(133) 3,9-bis-[(2,2,6,6-tetramethyl)-4-methoxy piperidine]-2,4,8,10-tetraoxa-3,9-di-phospha-spyro[5,5]undecane.

Among the above-cited compounds, compound (1) is described in Khim. Get. Soed. 1976 No. 7, pages 927-34 (E. I. Levkoeva, L. N. Iachontov), but there is not stated that this compound is useful as stabilizer for polymers.

The derivatives of 4-hydroxy-methyl-piperidine (I) are preparable according to conventional methods by means of the processes indicated hereinbelow.

Method A

The compounds of formula (I), where Y is hydrogen, are preparable by reduction of a compound of formula (III)

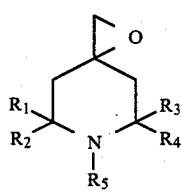

where $R_1$, $R_2$, $R_3$, $R_4$ and $R_5$ are defined as hereinbefore, by means of a reducing agent such as lithium or aluminum hydride with hydrogen and a catalyst such as the nickel Raney.

Method B

The compounds of formula (I), wherein Y is an acyl group, a group obtained by removing a hydroxy group from a phosphorus-containing acid, a diacyl group, a carbonyl X group, a group obtained by removing two hydroxy groups from a phosphorus-containing acid, the group

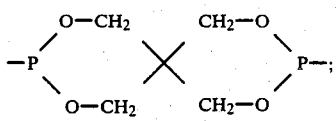

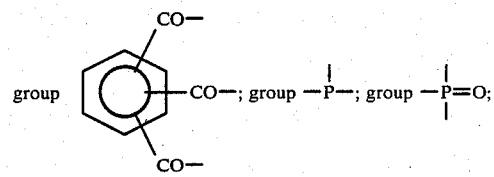

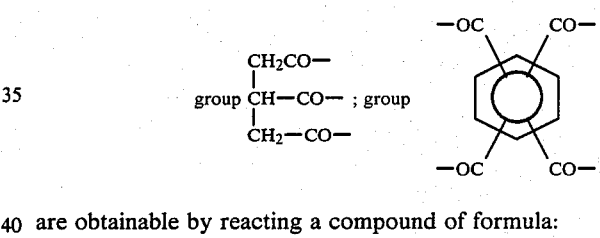

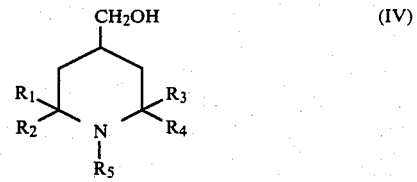

are obtainable by reacting a compound of formula:

$$\text{(IV)}$$

(wherein $R_1$, $R_2$, $R_3$, $R_4$ and $R_5$ are defined as hereinbefore) with a reactive derivative of the acid corresponding to group Y, for example with a halide or a lower alcohol ester.

Method C

The compounds of formula (I) in which Y represents an alkyl, alkenyl, aralkyl group, a cyclohexyl group, an alkylene group, an alkenyl group, a xylylene group, are preparable by reacting a compound of formula (IV), as already defined, with a halide of group Y.

Method D

The compounds of formula (I), wherein Y represents one of the groups —$CONHR_{22}$ or —$CONHR_{27}NH-CO-$, can be prepared by reacting a compound of formula (IV), as already defined, with an isocyanate of formula $R_{22}NCO$ or $OCN-R_{27}-N-CO-C$.

Method E

The compounds of formula (I), wherein Y represents one of the groups

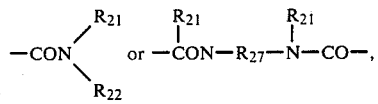

are preparable by reacting a compound of formula (IV), as already defined, with the carbamoyl chloride obtained by reacting phosgene on an amine of the type

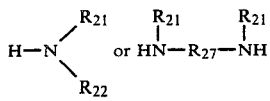

Method F

The compound of formula (I), in which Y represents the group —CO—$R_{20}$—COOH, are preparable by reacting the compound of formula (IV), as already defined, with an anhydride of formula:

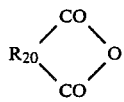

The esters and the salts of this group can be easily prepared according to conventional methods.

Method G

The compounds of formula (I), wherein Y represents a group

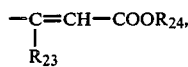

can be prepared by reacting a compound of formula (IV), as already defined, with a compound of formula $R_{23}$—C≡C—COOR$_{24}$.

Method H

The compounds of formula (I), where Y represents a group

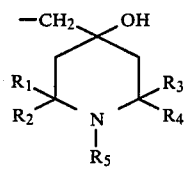

are preparable by reacting a compound of formula (IV), as already defined, with a compound of formula:

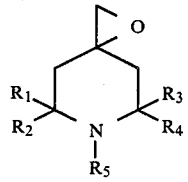

When $R_5$ is a group other than hydrogen, this can be introduced into the compound prior to or after the introduction of Y, by treating a compound of formula I, II, III or IV, where $R_5$ is the hydrogen atom, according to one of the following methods.

Method J

The compounds of formula I, II, III or IV, in which $R_5$ represents an alkyl group, an alkenyl group, an alkoxyalkyl group, an aralkyl group, a 2-3 epoxypropyl group, the group —$CH_2$—COO—$R_{10}$, the group

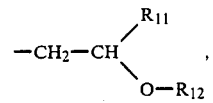

an aliphatic acyl group or the group —COOR$_{13}$ ($R_{10}$, $R_{11}$, $R_{12}$, $R_{13}$ and $R_{14}$ are the same as defined hereinbefore), are easy to prepare by reacting the corresponding compounds in which $R_5$ is a hydrogen atom with a halide of the group $R_5$.

Method K

The compounds of formula I, II, III or IV, in which $R_5$ represents the group

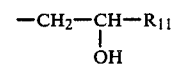

($R_{11}$ being defined as hereinbefore), can be prepared by reacting the corresponding compounds, in which $R_5$ is the hydrogen atom, with an epoxide, such as ethylene oxide, propylene oxide, styrene oxide. The resulting compounds can be acylated to obtain the corresponding acylated compounds.

Method L

The compounds of formula I, II, III or IV, in which $R_5$ represents a methyl group, are preparable according to the Leuckart-Wallach reaction, i.e., by reacting the corresponding compound, in which $R_5$ represents the hydrogen atom, with formic acid and formaldehyde.

Method M

The compounds of formula I, II, III or IV, in which $R_5$ represents a formyl group, can be prepared by reacting a corresponding compound, in which $R_5$ is a hydrogen atom, with ethyl orthoformate, in the presence of acid catalyst.

The compounds of formula III, which represent the starting substances for preparing the derivatives of 4-hydroxymethyl-piperidine having general formula (I), utilized in the polymeric compositions according to the present invention, can be prepared according to the teachings of U.S. Pat. No. 4,400,513.

The derivatives of 4-hydroxy-methyl piperidine having general formula (I) are useful to stabilize polymers, in particular synthetic polymers, against photo- and thermal degradation.

Examples of polymers which can be stabilized according to the present invention are:

polymers of olefins and of dienes, such as: homopolymers of olefins and of dienes (e.g., low density polyethylene, high density polyethylene and cross-linked polyethylene, polypropylene, polyisobutene, polymethylbutene-1, polymethylpentene-1, polyisoprene, polybutadiene), mixtures of such homopolymers or copolymers (for example, ethylene-propylene copolymers, propylene-butene-1 copolymers, or ethylene-propylene terpolymers and dienes, such as hexadiene, dicyclopentadiene), etc.;

styrene polymers, such as: polystyrene, copolymers of styrene and α-methylstyrene with acrylonitrile, methyl methacrylate, acrylic esters, styrene polymers modified with elastomers, grafted styrene polymers, etc.;

halogenated vinyl and vinylidene polymers, such as: vinyl polychloride, vinylidene polychloride, vinyl polyfluoride, polychloroprene, vinyl chloride/vinylidene chloride copolymers, vinyl chloride/vinyl acetate copolymers, vinylidene chloride/vinyl acetate copolymers, etc.;

polymers deriving from $\alpha$-$\beta$-unsaturated acids, such as: polyacrylates, polymethacrylates, polyacrylonitrile, polyacrylic amides;

polymers deriving from alcohols and from unsaturated amines and acylated or acetal derivatives thereof, such as polyvinyl alcohol, polyvinyl acetate, polyallyl melamine and copolymers thereof with other ethylenically unsaturated monomers;

epoxide polymers;

polyacetals;

polyurethanes and polyureas;

polycarbamates;

polysulphones;

polyamides and copolyamides;

polyesters;

cross-linked polymers, deriving from aldehydes and from phenols, from ureas or from melamines;

alkyd resins;

unsaturated polyester resins;

natural polymers, such as cellulose, rubber, proteins or chemically modified analogues thereof (e.g., cellulose acetate), etc.

The proportion of 4-hydroxy-methyl-piperidine of formula (I) necessary to efficaciously stabilize the polymers depends on various factors, such as the type and properties of the polymer, the use for which it is intended, the simultaneous presence of other stabilizers.

Generally, such amounts range from 0.01 to 5% by weight of stabilizer referred to the polymer.

In particular, the preferred amount ranges from 0.02 to 1% for the polymers of olefins, dienes and styrene, from 0.02 to 0.5% for the polymers of vinyl and vinylidene, from 0.02 to 2% for polyurethanes and polyamides.

Optionally, two or more stabilizers having general formula (I) can be utilized.

The derivatives of 4-hydroxymethyl piperidine of formula (I) utilized as stabilizers in the polymeric compositions according to this invention can be easily incorporated into the polymers to be stabilized, according to conventional operating methods, e.g., the stabilizers can be mixed with the polymer in the form of a dry powder, or a stabilizer solution or suspension or emulsion can be admixed to a polymer solution or suspension or emulsion.

The derivatives of the alkyl-substituted 4-hydroxymethyl-piperidine of formula (I) can be employed either alone or in admixture with other known additives such as antioxidants, UV-ray absorbers, pigments, fillers, basic nitrogenous polycondensates, stabilizers and the like.

Examples of such additives are oxybenzotriazoles, oxobenzophenones, Ni stabilizers, metal soaps, phenolic antioxidants, phosphites, phosphinites, thioesters, hydroquinone derivatives, triazinic compounds, acylamino-phenols, benzyl-phosphates, sterically hindered phenols such as 4,4′-bis-butylidene-bis-(2,6-di-tert.butyl-phenol); triazino-phenol compounds, etc.

Such additives can be utilized along with the compounds having formula (I), according to the present invention, in a weight ratio ranging from 0.5:1 to 3:1.

For a better understanding of the present invention and as aid to practicing the same, there are reported hereinbelow a few illustrative preferred examples which are not considered a limitation of the invention.

In the examples, all parts are indicated by weight, unless otherwise specified.

EXAMPLE 1

Preparation of 2,2,6,6-tetramethyl-4-hydroxymethyl-piperidine (compound No. 1)

134.4 g of 2,2,6,6-tetramethyl piperidyl-4-spyrooxirane (0.8 moles) in 500 cc of ethanol and 15 g of Ni/Raney were charged into a steel autoclave equipped with a magnetic stirrer.

Hydrogen was charged up to a pressure of 50 atm. and the temperature was brought to 120° C. The reaction mixture was maintained at the indicated temperature during 6 hours.

It was cooled down, the catalyst was filtered, the solvent was evaporated and the residue was placed in an oven under vacuum at 100° C./1 mmHg of residual pressure. There were obtained 125 g of product having a melting point of 172°–174° C. and a gas-chromatographic titer [on a Supelco column (registered trademark) SP 1000] higher than 99%. The yield was 91.4%.

The product was characterized by N.M.R. and I.R. analyses and recognized as the product intended to be obtained.

EXAMPLE 2

By operating according to the same piperidyl modalities of Example 1, from 1,2,2,6,6-pentamethyl-piperidyl-4-spyro-oxirane there was obtained 1,2,2,6,6-pentamethyl-4-hydroxymethyl piperidine having a M.P. of 84°–85° C. (compound No. 22).

EXAMPLE 3

Preparation of (1-2-hydroxyethyl)-2,2,6,6-tetramethyl-4-hydroxymethyl-piperidine (compound No. 38)

25 g of 2,2,6,6-tetramethyl-4-hydroxymethyl-piperidine of Example 1 (0.146 moles) were dissolved in 50 cc of methanol and added with 8 g (0.18 moles) of ethylene oxide. The solution was introduced into a steel autoclave and heated under stirring during 6 hours at 120° C. Then the solvent was evaporated and the residue was crystallized from acetonitrile. 30 g of product having a M.P. of 81°–83° C. were obtained, the product being characterized by N.M.R. and I.R. analyses and recognized as the product intended to be obtained.

EXAMPLE 4

Preparation of bis(2,2,6,6-tetramethyl)-4-methyl-piperidine adipate (compound No. 79)

Into a flask there were introduced 20.5 g of 2,2,6,6-tetramethyl-4-hydroxymethyl piperidine of Example 1 (0.12 moles), 10.45 of methyl adipate (0.06 moles) and 0.5 g of LiOH in 100 cc of xylene. The temperature inside the flask was brought to 140° C. and at the top of a rectification column the methyl alcohol coming from the reaction was distilled.

Once all the theoretically calculated alcohol had been distilled, the whole was brought to dryness by distilling xylene under vacuu. $CH_2Cl_2$ and water were added to the residue and the organic layer was separated from the aqueous layer.

The dried organic layer was evaporated from the solvent and the residue was diluted again in hot conditions with acetone. There were obtained 25 g of product having a M.P. of 97°–98° C., which was characterized by means of N.M.R. and I.R. analyses and recognized to be the product intended to be obtained.

EXAMPLES 5 TO 14

By operating under the same conditions as described in Example 4, the following products were prepared:

| Compound No. | Name | M.P. |
| --- | --- | --- |
| 17 | 2,2,6,6-tetramethyl-4-methyl piperidine β(4-hydroxy-3,5-ditert.butyl phenyl propionate | 76–78° C. |
| 3 | 2,4,6,6-tetramethyl-4-methyl piperidine palmitate | thick fluid |
| 80 | bis-[(2,2,6,6-tetramethyl)-4-methyl piperidine] sebacate | 58–59° C. |
| 81 | bis-[(2,4,6,6-tetramethyl)-4-methyl piperidine] (3,5-ditert.butyl-4-hydroxy)benzyl-n.butyl malonate | 97–99° C. |
| 82 | bis-[(2,2,6,6-tetramethyl)-4-methyl piperidine] diethylmalonate | thick fluid |
| 84 | bis-[(2,2,6,6-tetramethyl)-4-methyl piperidine] terephthalate | 120–121° C. |
| 88 | bis-[(1,2,2,6,6-pentamethyl)-4-methyl piperidine] sebacate | liquid |
| 27 | (1,2,2,6,6-pentamethyl-4-methyl piperidine) β(4-hydroxy-3,5-ditert. butyl phenyl) propionate | 73–75° C. |
| 126 | tetra-kis-[(1,2,2,6,6-pentamethyl)-4-methyl piperidine] pyromellitate | 154–157° C. |
| 89 | bis-[(1,2,2,6,6-pentamethyl)-4-methyl piperidine] terephthalate | 146–147° C. |

EXAMPLE 15

Preparation of 1-(2-stearoyloxyethyl)-2,2,6,6-tetramethyl-4-methyl piperidine stearate (compound No. 43)

9.8 g of 1-(2-hydroxyethyl)-2,2,6,6-tetramethyl-4-hydroxymethyl piperidine as obtained in Example 2 (0.045 mole) were admixed to 28.7 g of methyl stearate (0.09 mole) in the presence of 0.5 g of LiOH. The mixture was heated to 140° C. in a nitrogen atmosphere and was maintained under stirring until complete evolvement of the reaction methyl alcohol.

The reaction mass was diluted again with $CH_2Cl_2$ and washed with $H_2O$. After removal of solvent from the organic layer, the residue was crystallized from acetone. 29 g of product having a melting point of 50°–52° C. were obtained.

The product was recognized from the I.R. and N.M.R. spectra.

EXAMPLE 16

By operating according to Example 15, [1-(2-palmithoxyethyl)-2,2,6,6-tetramethyl] piperidine palmitate (compound No. 45) was prepared. The product was liquid.

EXAMPLE 17

Preparation of mono (1,2,2,6,6-pentamethyl-4-methyl piperidine succinate) (compound No. 90)

62 g of 1,2,2,6,6-pentamethyl-4-hydroxymethyl piperidine (compound No. 22) (0.335 mole) and 33.5 g of succinic anhydride (0.335 mole) were dissolved in 300 cc of benzene and the solution was brought to the reflux temperature of the solvent. After half an hour, it was cooled down and the precipitate was filtered, thus obtaining 85 g of product having a M.P. of 186°–189° C., which was recognized by means of I.R. and N.M.R. analyses as the product intended to be obtained.

EXAMPLES 18–19

By operating according to the modalities of Example 17, there were prepared:
mono (1,2,2,6,6-pentamethyl)-4-methyl piperidine-3,4,5,6-tetrahydrophthalate, having a M.P. of 182°–185° C. (compound No. 91); and
mono (2,4,6,6-tetramethyl)-4-methyl piperidine maleate, having a M.P. of 245°–248° C. (compound No. 92).

EXAMPLE 20

Preparation of nickel di-[mono (1,2,2,6,6-pentamethyl)-4-methyl piperidine succinate] (compound No. 98)

14.27 g of compound No. 90 of Example 17 (0.05 mole) were dissolved in 50 cc of methanol and added with 2.8 g of KOH (0.05 mole) and, by slowly dropping, in half an hour, with 5.94 g of $NiCl_2.6H_2O$, dissolved in 20 cc of methanol.

On conclusion of the dropping, the temperature was raised up to solvent reflux during 2 hours. It was cooled down and the KCl which had formed was filtered. The solvent was evaporated and the residue was diluted with benzene. The insoluble portion was filtered and the solution was evaporated to dryness.

The residual green solid product had a M.P. of 149°–154° C. and, subjected to elemental analysis, revealed a Ni content=9.4% (theoretical value=9.36% for the desired product).

EXAMPLE 21

By operating under the same conditions of Example 6, nickel di-[3,4,5,6-tetrahydrophthalate of mono (1,2,2,6,6-pentamethyl)-4-methyl piperidine] (compound No. 93) was prepared. It was a green solid having a M.P. of 154°–157° C.

EXAMPLE 22

Preparation of bis[(1,2,2,6,6-pentamethyl)-4-methyl piperidine]hexamethylene di-carbamate (compound No. 108)

Into a flask there were introduced 19.8 g (0.107 mole) of compound No. 22 of Example 2, in 100 cc of ethyl acetate, and to the solution under stirring there were added 9 g (0.0535 mole) of hexamethylene diisocyanate dissolved in 50 cc of ethyl acetate. Stirring was continued for 4 hours, while raising the temperature up to solvent reflux.

The solvent was evaporated under vacuum and the residue was diluted with acetonitrile. A solid product having a melting point of 48°–50° C., which was recognized under N.M.R. and I.R. analyses, was obtained.

EXAMPLE 23

Preparation of

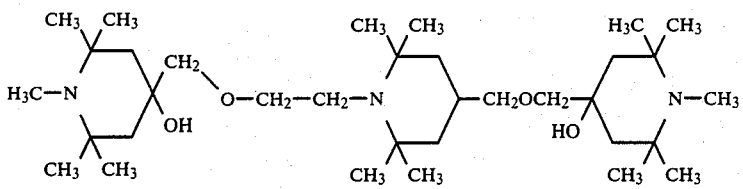

(compound No. 117).

23 g of 1,2,2,6,6-pentamethyl-piperidyl-4-spyrooxirane (0.126 mole) were reacted with 12.9 g of compound No. 38 (0.06 mole) at 140° C. during 3 hours in the presence of 0.5 g of KOH. The reaction mass was then diluted with $CH_2Cl_2$ and washed with water.

The dried organic layer was evaporated off from the solvent and the residue was diluted with acetone. There were obtained 30 g of product having a M.P. of 124°–126° C., which was characterized by N.M.R. and I.R. analyses and recognized as the product to be obtained.

EXAMPLE 24

By operating as in Example 23, [(2,2,6,6-tetramethyl-4-hydroxy)-4-piperidinmethoxy] (2,2,6,6-tetramethyl)-4-methyl piperidine was prepared

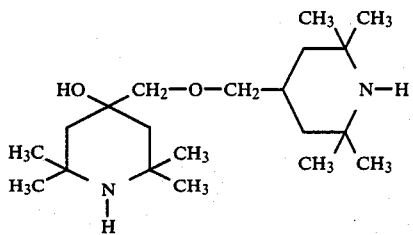

White solid having a melting point of 65°–67° C. (compound No. 69).

EXAMPLE 25

Preparation of 1,6 bis[(2,2,6,6-tetramethyl)-4-piperidinmethoxy]hexane (compound No. 113)

34.2 g (0.2 mole) of compound No. 1 obtained in Example 1 were put into 200 cc of xylene. 4.6 g of sodium metal (0.2 g.a.) were gradually added, under stirring, to the solution.

Successively, to the solution there were added dropwise 33.8 g of di-iodohexane (0.1 mole). It was heated until solvent reflux, and these conditions were maintained for 8 hours.

Water was added and the organic layer, after separation and drying, was evaporated from the solvent.

The residue was crystallized from acetone. 32 g of a solid product having a melting point of 69°–70° C. were obtained, the product being characterized by N.M.R. and I.R. analyses and recognized as the product intended to be obtained.

EXAMPLE 26

By operating under the same conditions as described in Example 9, 1,4-bis[(2,2,6,6-tetramethyl)-4-piperidine methoxy]butane (compound No. 111) was prepared.

The product obtained was solid and had a M.P. of 68°–69° C.

EXAMPLE 27

Preparation of 3,9-bis-[(2,2,6,6-tetramethyl)-4-methoxy piperidine]-2,4,8,10-tetraoxa-3,9-di-phospha-spyro-[5,5]undecane. (compound No. 133)

18.52 g of compound No. 1 as obtained in Example 1 (0.1083 mole) was dissolved in 150 cc of xylene. To the resulting solution there were gradually added, under stirring, 2.55 g of sodium metal (0.11 g.a.) and, successively, 13.25 g of (2,4,8,10-tetraoxa-3,9-diphospho)-spyro[5,5]undecane 3,9 di-chloro (0.05 mole). It was heated up to solvent reflux during 8 hours. At the end of heating, water was added and the organic layer was separated, dried and evaporated from the solvent. The residue was diluted with hexane and was crystallized.

20 g of product having a melting point of 99°–101° C. were obtained, the product being characterized by N.M.R. and I.R. analyses and recognized as the product to be obtained.

EXAMPLE 28

Stabilization tests

To 300 g of non-stabilized polypropylene, having an intrinsic viscosity, measured at 130° C. in tetralin, of 162 cc/g, a residue of 96.5% of the extraction with heptane and an ash content of 80 ppm, there were added 200 cc of chloroform containing, dissolved therein, one of the compounds reported in the table. The added compound amount was of 0.5% by weight referred to polypropylene.

The mixture was stirred during about 6 hours, at room temperature, in a rotary evaporator, then it was dried at 0.01 mm of Hg and at 50° C. for 1 hour. The resulting additioned powder was extruded in a Brabender extruder at 220° C. and granulated. The granules were transformed to films having a uniform thickness of 50–60 microns.

On the films so obtained there was determined the photo-oxidative stability, considered as the time required to obtain rupture of the film, by one bending by 180°, after exposure to Zenotest 1200 under the following conditions:
black panel temperature: 43±2° C.
relative humidity: 50±5%
alternate exposure.

The obtained results were:

| Compound No. | Embrittlement time in hours |
| --- | --- |
| — | 100 |
| 3 | 2250 |
| 17 | 2600 |
| 43 | 2300 |
| 45 | 2200 |
| 79 | 3800 |
| 80 | 4200 |
| 81 | 3600 |

-continued

| Compound No. | Embrittlement time in hours |
|---|---|
| 82 | 3800 |
| 84 | 3500 |
| 89 | 3200 |
| 98 | 4000 |
| 111 | 3800 |
| 113 | 4100 |
| 117 | 3700 |
| 126 | 3200 |
| 133 | 3000 |

We claim:

1. Derivatives of alkyl-substituted 4-hydroxy-methyl piperidine having the formula:

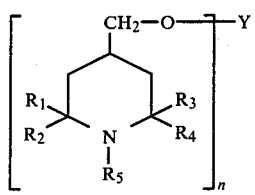

wherein:

$R_1$, $R_2$, $R_3$ and $R_4$, the same or different, are each a $C_1$–$C_6$ alkyl group, or $R_1$ and $R_2$ and/or $R_3$ and $R_4$, together with the carbon atoms to which they are bound, represent a $C_5$–$C_7$ cycloalkyl group or a group of the formula:

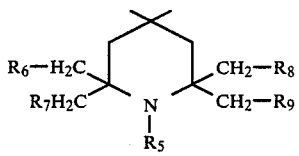

in which $R_6$, $R_7$, $R_8$ and $R_9$, the same or different, represent a hydrogen atom or a $C_1$–$C_6$ group and $R_5$ has the meaning defined below;

$R_5$ represents a hydrogen atom, a $C_1$–$C_8$ alkyl group, a $C_3$–$C_6$ alkenyl group, an alkoxyalkyl group containing 1-3 carbons in the alkyl chain and 1-18 carbons in the alkoxyl chain, a $C_7$–$C_8$ aralkyl group, a substituted aralkyl group carrying 1 to 3 substituents on the aryl radical, said substituents being selected from the group consisting of chlorine, $C_1$–$C_4$ alkyl, $C_1$–$C_8$ alkyl and hydroxy, a 2,3-epoxypropyl group, a group of formula —CH$_2$—COOR$_{10}$, in which $R_{10}$ is a $C_1$–$C_{18}$ alkyl group, a $C_3$–$C_8$ alkenyl group, a phenyl group, a $C_7$–$C_8$ aralkyl group or a cyclohexyl group; a group of the formula:

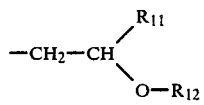

in which $R_{11}$ is a hydrogen atom, a methyl group, an ethyl group or a phenyl group and $R_{12}$ is a hydrogen atom, a $C_1$–$C_6$ alkyl substituted piperidyl group, a triazinyl group or an acyl group of formula —COR$_{18}$ in which $R_{18}$ is a $C_1$–$C_{18}$ alkyl group, a $C_2$–$C_4$ alkenyl group, a phenyl group having 1 to 3 substituents, a $C_7$–$C_8$ aralkyl group, a $C_1$–$C_6$ alkoxy group, a styryl group, or a cyclohexyl group; a $C_1$–$C_4$ aliphatic acyl group or a group of formula —COOR$_{13}$ in which $R_{13}$ is a $C_1$–$C_{18}$ alkyl group, a benzyl group or a phenyl group;

Y represents a hydrogen atom or an organic or inorganic group or atom having a valence ranging from 1 to 4 which does not adversely affect the polymer-stabilization activity; and n is an integer ranging from 1 to 4, depending on the valence of Y.

2. A compound according to claim 1, in which each of $R_1$, $R_2$, $R_3$ and $R_4$ is an alkyl group containing from 1 to 4 carbon atoms.

3. A compound according to claim 1, in which $R_1$ and $R_2$ and/or $R_3$ and $R_4$, together with the carbon atoms to which they are bound, represent a cycloalkyl group containing from 5 to 7 carbon atoms, or

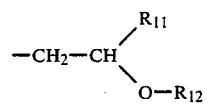

4. A compound according to claim 1, in which $R_5$ is selected from the following groups:

an alkyl group containing 1 to 4 carbon atoms;

an alkenyl group containing 3 to 6 carbon atoms;

an alkoxy-alkyl group containing 1 to 3 carbon atoms in the alkyl chain and 1 to 18 carbon atoms in the alkoxyl chain;

an aralkyl group containing 7 or 8 carbon atoms, such an aralkyl group substituted in the alkyl radical by up to 3 substituents selected from chlorine atoms, alkyl groups containing 1 to 4 carbon atoms, alkoxy groups containing 1 to 8 carbon atoms and hydroxy groups;

a group of formula —CH$_2$—COOR$_{10}$ in which $R_{10}$ is an alkyl group containing 1 to 18 carbon atoms, an alkenyl group containing 3 to 6 carbon atoms, an aralkyl group containing 7 or 8 carbon atoms or a cyclohexyl group;

a group $$-CH_2-CH\begin{array}{c}R_{11}\\O-R_{12}\end{array}$$

in which $R_{11}$ is hydrogen, methyl or phenyl and $R_{12}$ is hydrogen;

a group of formula

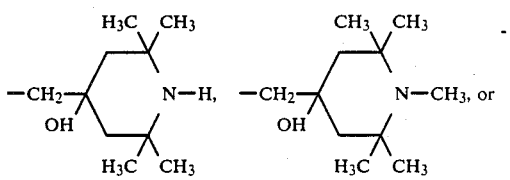

-continued

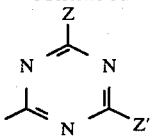

in which Z and Z', the same or different, represent hydrogen, —NR$_{14}$R$_{15}$, —O—R$_{16}$ or —S—R$_{17}$ in which R$_{14}$, R$_{15}$, R$_{16}$ and R$_{17}$ may be hydrogen, an alkyl radical containing 1 to 18 carbon atoms or an alkyl-substituted piperidyl group of formula:

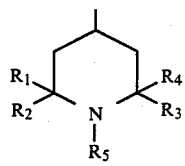

or R$_{14}$ and R$_{15}$ together with the N atom form a cycle containing or not containing the other heteroatoms

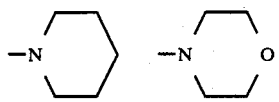

or R$_{12}$ represents an acyl group —COR$_{18}$ in which R$_{18}$ represents an alkyl group containing 1 to 18 carbon atoms, an alkenyl group with 2 to 4 carbon atoms; a phenyl group, phenyl substituted by up to 3 substituents, either like or unlike one another and selected from chlorine, alkyl with 1 to 4 carbon atoms, alkoxy with 1 to 8 carbon atoms or hydroxy; an aralkyl group with 7 or 8 carbon atoms, an aralkyl group substituted on the aryl radical by up to 3 substituents, like or unlike one another and selected from chlorine, alkyl with 1 to 4 carbon atoms, alkoxy with 1 to 8 carbon atoms or hydroxy; a styryl group, or a cyclohexyl group;
a group of formula —COOR$_{13}$ in which R$_{13}$ represents an alkyl group, a benzyl group or a phenyl group.

5. A compound according to claim 1, in which Y is a hydrocarbon radical, a substituted hydrocarbon radical, a radical deriving from an organic or inorganic acid, a heterocyclic group, a phosphorus atom, a boron atom or a silicon atom.

6. A compound according to claim 5, in which Y represents:
when n<1
an acylaliphatic, arylaliphatic, alicyclic, aromatic or heterocyclic group, a group of formula —COR$_{19}$ in which R$_{19}$ represents a hydrogen atom, an alkyl group with 1 to 17 carbon atoms; an alkenyl group with 2 to 5 carbon atoms; an alkynyl group with 2 to 3 carbon atoms; a phenyl group, a substituted phenyl group with up to 3 substituents, like or unlike and selected from chlorine, alkyl with 1 to 4 carbon atoms, alkoxy with 1 to 8 carbon atoms, hydroxy or nitro; a naphthyl group; a styryl group, an aralkyl group with 7 or 8 carbon atoms, a substituted aralkyl group with up to 3 like or unlike substituents selected from chlorine, alkyl with 1 to 4 carbon atoms, alkoxy with 1 to 8 carbon atoms or hydroxy; a phenoxymethyl group, a cyclohexyl group, a 2-pyridyl group; a 3-pyridyl group; a 4-pyridyl group; a 2-furyl group;
a group of formula —CO—R$_{20}$—COOH, in which R$_{20}$ represents an alkylene group the chain of which can be interrupted by an atom of oxygen or of sulphur; or a metal salt thereof, in which the metal is selected from barium, nickel, manganese, calcium, zinc, iron, sodium, cobalt and tin; or a lower alkyl ester thereof in which the alkyl chain contains 1 to 4 carbon atoms;
a radical resulting from the removal of a hydroxyl group of a phosphorus acid, and which may be a radical of phosphoric acid, of phosphonic acid or of phosphorous acid, either simple or substituted and selected from:

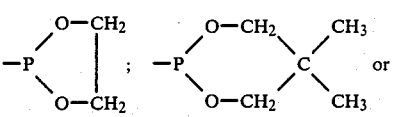

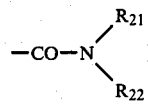

a group of formula:

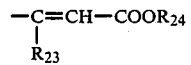

in which R$_{21}$ represents hydrogen; an alkyl group containing 1 to 4 carbon atoms; an aralkyl group containing 7 or 8 carbon atoms; a phenyl group; and R$_{22}$ represents an alkyl group containing 1 to 18 carbon atoms, an aryl group containing from 6 to 10 carbon atoms, optionally substituted by one or more chlorine atoms and/or alkyl groups with 1 to 4 carbon atoms; an aralkyl group containing 7 or 8 carbon atoms; a cyclohexyl group; or R$_{21}$ and R$_{22}$, together and with the nitrogen atom to which they are bound, form a piperidinic group, a 1-pyrrolidinyllic group or a morpholinic group;
an alkyl group containing 1 to 18 carbon atoms;
an alkynyl group containing 3 to 6 carbon atoms;
an aralkyl group with 7 to 9 carbon atoms, an aralkyl group carrying up to 3 substituents in the aryl chain selected from an alkyl with 1 to 4 carbon atoms and/or a hydroxyl group;
a cyclohexyl group;
a group of formula:

$$-\underset{R_{23}}{C}=CH-COOR_{24}$$

in which R$_{23}$ represents a hydrogen atom, a methyl or lower alkyl group or a phenyl group and R$_{24}$ represents an alkyl group containing 1 to 8 carbon atoms;
when n=2 an aliphatic, araliphatic, aromatic, alicyclic or heterocyclic diacyl group containing up to 12 carbon atoms;

an alkenyl group with 2 to 4 carbon atoms; a phenylene group;

a cyclohexylene group; a 2,4-pyridindiyl group, a 2,5-pyrindindiyl group, or a thiophendiyl group;

a carbonyl group;

a group obtained by removing two hydroxyl groups of an acid containing phosphorus and having the formula:

$$=P-R_{26} \quad \text{or} \quad =\overset{O}{\overset{\|}{P}}-R_{26}$$

in which $R_{26}$ represents a hydrogen atom; an alkyl group with 1 to 4 carbon atoms; a phenyl or benzyl group, optionally substituted;

a group of formula:

$$-P\begin{matrix}O-CH_2 \\ O-CH_2\end{matrix}\times\begin{matrix}CH_2-O \\ CH_2-O\end{matrix}P-$$

a group of formula:

$$-CO-\overset{R_{21}}{\underset{|}{N}}-R_{27}-\overset{R_{21}}{\underset{|}{N}}-CO-$$

in which $R_{21}$ has the same meaning as defined herein and $R_{27}$ represents an alkylene group containing 2 to 10 carbon atoms; an arylene group having 6 to 10 carbon atoms and optionally substituted, a xylylene group, a cyclohexylene group, a group of formula:

[phenyl–R_{28}–phenyl structure]

in which $R_{28}$ may be an atom of oxygen or an alkylene group containing 1 to 4 carbon atoms; a group of formula:

[R_{29}-biphenyl-R_{29} structure]

in which $R_{29}$ may be a hydrogen atom or a methyl group, a group of formula:

[cyclohexyl–CH_2–cyclohexyl structure]

or a group of formula:

[–CH_2–cyclohexylene–CH_2– structure]

an alkylene group containing up to 10 carbon atoms; or a xylylene group;

when n=3

Y is selected from the following radicals:

[benzene tri-CO– structure]; $-\overset{|}{\underset{|}{P}}-$; $-\overset{|}{\underset{|}{P}}=O$; $-\overset{|}{B}-$ when n=4

Y is

[benzene tetra(–OC/CO–) structure] or $-\overset{|}{\underset{|}{Si}}-$.

7. A compound according to claim 1, characterized by having general formula:

$$\left[\begin{matrix} \text{CH}_2\text{O}\text{———}\\ \text{H}_3\text{C}\underset{\underset{R_5}{N}}{\diagup}\text{CH}_3 \\ \text{H}_3\text{C}\diagdown\quad\diagup\text{CH}_3 \end{matrix}\right]_n\text{———Y} \quad (II)$$

in which $R_5$ represents a hydrogen atom, a methyl group, a benzyl group, a 2,3-epoxypropyl group or a group of formula $-CH_2-CH_2-O-R_{12}$ in which $R_{12}$ is hydrogen or an alkyl group with 2 to 18 carbon atoms or a benzoyl group; n=1, 2 or 3; and when n=1

Y represents a group of formula $-CO-R_{19}$ in which $R_{19}$ represents an alkyl group with 1 to 17 carbon atoms, a phenyl group optionally substituted by up to 3 alkyl radicals containing 1 to 4 carbon atoms and/or a hydroxy group, or a 4-hydroxy-3,5-di-tert.butylphenethyl group; or a group of formula $-CO-NH-R_{22}$ in which $R_{22}$ represents an alkyl group with 1 to 18 carbon atoms, a phenyl group or a cyclohexyl group;

when n=2

Y represents a group of formula $-CO-(R_{25})_m-CO-$ in which m is 0 or 1 and $R_{25}$ represents an alkenyl group with 1 to 10 carbon atoms; the group $-CH_2-CH_2-S-CH_2-CH_2$ or a phenylene group, a group of formula

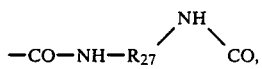

in which $R_{27}$ represents the hexamethylene radical, 2,4-toluylene or methylene-di-p.phenylene;
when $n=3$
Y represents

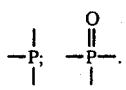

8. A compound according to claim 7, in which in general formula (II)
$n=1$ and Y represents a group of formula $-CO-R_{19}$; or
$n=2$ and Y represents a group of formula $-CO-R_{25}-CO$, with $R_{19}$ and $R_{25}$ having the same meanings as defined herein.

9. A compound according to claim 4, in which $R_5$ is the group $-COOR_{13}$ in which $R_{13}$ is an alkyl radical containing from 1 to 8 carbon atoms.

10. A compound according to claim 6, in which, when n is 1, Y is an acyl group containing up to 18 carbon atoms.

11. A compound according to claim 6, in which, when n is 1, Y is a group of formula $-CO-R_{20}-COOH$ in which $R_{20}$ is an alkylene group containing 1 to 10 carbon atoms.

12. A compound according to claim 6 in which, when n is 2, Y is a group of formula $-CO-(R_{25})_m$ in which m is 0 or 1 and $R_{25}$ is a linear or ramified alkylene radical containing up to 20 carbon atoms and which may contain an alkylbenzyl or hydroxyalkyl benzyl group, and the chain of which group $R_{25}$ can be interrupted by an atom selected from the group consisting of sulphur and oxygen atoms.

13. A compound having the formula

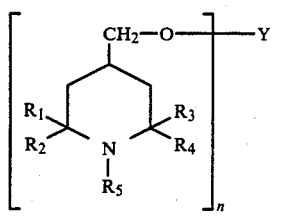

(I)

in which
$R_1$, $R_2$, $R_3$ and $R_4$, the same or different, are each a $C_1$–$C_6$ alkyl group, or $R_1$ and $R_2$ and/or $R_3$ and $R_4$, together with the carbon atoms to which they are bound, are selected from the group consisting of $C_5$–$C_7$ cycloalkyl and groups of the formula

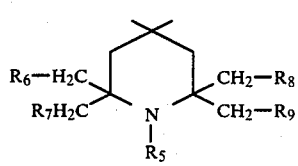

(II)

in which $R_6$, $R_7$, $R_8$ and $R_9$, the same or different, are selected from the group consisting of hydrogen and $C_1$–$C_6$ alkyl; and $R_5$ is selected from the group consisting of
(1) hydrogen,
(2) $C_1$–$C_8$ alkyl,
(3) $C_3$–$C_6$ alkenyl,
(4) alkoxyalkyl containing 1 to 3 carbon atoms in the alkyl chain and from 1 to 18 carbon atoms in the alkoxyl chain,
(5) $C_7$–$C_8$ aralkyl,
(6) $C_7$–$C_8$ aralkyl carrying 1 to 3 substituents on the alkyl radical, said substituents being selected from the group consisting of chlorine, $C_1$–$C_4$ alkyl, $C_1$–$C_8$ alkoxy, and hydroxy;
(7) a group of formula

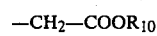

in which $R_{10}$ is selected from the group consisting of $C_1$–$C_{18}$ alkyl, $C_3$–$C_6$ alkenyl, $C_7$–$C_8$ aralkyl, and cyclohexyl;
(8) the group

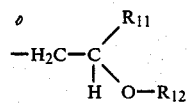

in which $R_{11}$ is selected from the group consisting of hydrogen, methyl and phenyl and $R_{12}$ is selected from the group consisting of hydrogen, an acyl group of formula $-COR_{18}$ in which $R_{18}$ is selected from the group consisting of $C_1$–$C_{18}$ alkyl, $C_2$–$C_4$ alkenyl, phenyl, phenyl substituted by 1 to 3 substituents selected from the group consisting of chlorine, $C_1$–$C_4$ alkyl, $C_1$–$C_8$ alkoxy, hydroxy, $C_7$–$C_8$ aralkyl, $C_7$–$C_8$ aralkyl in which the aryl radical is substituted by 1 to 3 substituents which are the same or different and selected from the group consisting of chlorine, $C_1$–$C_4$ alkyl, $C_1$–$C_6$ alkoxy, hydroxy, styryl and cyclohexyl;
(9) a group having one of the formula

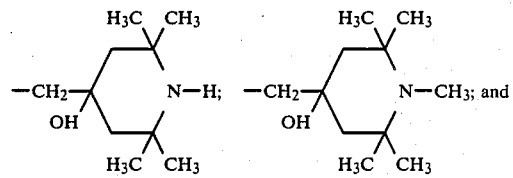

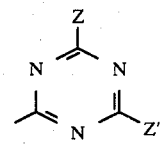

in which Z and Z', the same or different, are selected from the group consisting of hydrogen, $-R_{14}R_{15}$, $-O-R_{16}$ and $-S-R_{17}$ in which $R_{14}$, $R_{15}$, $R_{16}$ and $R_{17}$ are selected from the group consisting of hydrogen, $C_1$–$C_{18}$ alkyl, a $C_1$–$C_6$-substituted piperidyl group of the formula

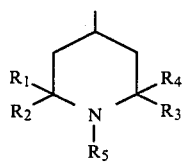

and groups in which $R_{14}$ and $R_{15}$, together with the N atom, form a cycle which may contain other heteroatoms selected from O and S atoms;
(10) a group of formula —$COOR_{13}$, in which $R_{13}$ is selected from the group consisting of $C_1$-$C_8$ alkyl, benzyl and phenyl;
n is an integer from 1 to 4 depending on the valence of Y; and when n is 1, Y is selected from
(11) the group consisting of groups of formula —CO—$R_{19}$ in which $R_{19}$ is selected from the group consisting of $C_1$-$C_{17}$ alkyl, phenyl, phenyl substituted by one to three $C_1$-$C_4$ alkyl radicals and/or a hydroxy radical, 4-hydroxy-3,5-di-tert-.butylphenethyl, and groups of formula —CO—NH—$R_{22}$ in which $R_{22}$ is selected from the group consisting of $C_1$-$C_{18}$ alkyl, phenyl and cyclohexyl;
when n is 2, Y is selected from
(12) the group consisting of groups of formula —CO—$(R_{25})_m$—CO— in which m is zero or 1 and $R_{27}$ is selected from the group consisting of $C_1$-$C_{10}$ alkenyl, the grouup —$CH_2$—$CH_2$—S—$CH_2$—$CH_2$, phenylene and a group of formula

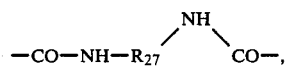

in which $R_{27}$ is a radical selected from the group consisting of hexamethylene, tolulene and methylene-di-p-phenylene;
when n is 3, Y is selected from
(13) the group consisting of the radicals

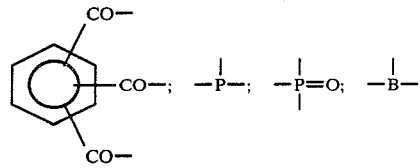

and
when n is 4, Y is selected from
(14) the radicals

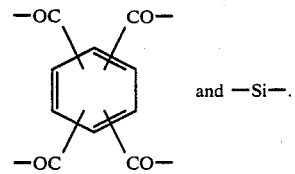

14. A compound according to claim 1, and which is bis-(2,2,6,6-tetramethyl)-4-methyl piperidine adipate.

15. bis-(2,2,6,6-tetramethyl)-4-methyl piperidine sebacate.

16. A compound according to claim 1, and which is bis-(2,2,6,6-tetramethyl)-4-methyl piperidine diethyl malonate.

17. A compound according to claim 1, and which is nickel-di-[succinate of mono-(1,2,2,6,6-pentamethyl)-4-methyl piperidine].

18. A compound according to claim 1, and which is 1,4 bis[(2,2,6,6-tetramethyl)-4-piperidine methoxy]butane.

19. A compound according to claim 1, and which is 1,2 bis[(2,2,6,6-tetramethyl)-4-piperidine methoxy]hexane.

* * * * *